United States Patent
Andersen

[11] Patent Number: 5,993,755
[45] Date of Patent: Nov. 30, 1999

[54] DISINFECTION SYSTEM FOR DISINFECTION OF CONTACT LENSES

[76] Inventor: Thorkild Andersen, Siriusvej 13, DK-8370 Hadsten, Denmark

[21] Appl. No.: 08/875,117

[22] PCT Filed: Jan. 23, 1996

[86] PCT No.: PCT/DK96/00036

§ 371 Date: Oct. 17, 1997

§ 102(e) Date: Oct. 17, 1997

[87] PCT Pub. No.: WO96/22927

PCT Pub. Date: Aug. 1, 1996

[30] Foreign Application Priority Data

Jan. 23, 1995 [DK] Denmark .................................. 0075/95

[51] Int. Cl.⁶ ................................ A61L 2/18; B65D 81/22
[52] U.S. Cl. ............................. 422/300; 422/292; 206/5.1; 134/901
[58] Field of Search ................................ 422/28, 40, 292, 422/300, 301; 206/5.1; 134/901

[56] References Cited

U.S. PATENT DOCUMENTS

| | | | |
|---|---|---|---|
| 4,429,786 | 2/1984 | Hucal | 206/5.1 |
| 4,852,592 | 8/1989 | DiGangi et al. | 206/5.1 |
| 5,053,208 | 10/1991 | Seamons et al. | 422/300 |
| 5,164,166 | 11/1992 | Stepanski et al. | 422/301 |
| 5,167,323 | 12/1992 | Ohta et al. | 206/5.1 |
| 5,181,604 | 1/1993 | Ohta et al. | 206/5.1 |
| 5,275,784 | 1/1994 | Perlaky | 422/28 |
| 5,375,698 | 12/1994 | Ewart et al. | 206/5.1 |
| 5,396,984 | 3/1995 | Wanders | 206/5.1 |
| 5,467,868 | 11/1995 | Abrams et al. | 206/5.1 |
| 5,598,919 | 2/1997 | Taylor | 206/5.1 |
| 5,605,667 | 2/1997 | Powell | 422/301 |
| 5,609,246 | 3/1997 | Borghorst et al. | 206/5.1 |
| 5,657,506 | 8/1997 | Pankow | 206/5.1 |

FOREIGN PATENT DOCUMENTS

| | | |
|---|---|---|
| 0 401 163A1 | 5/1990 | European Pat. Off. . |
| 0 381 616A1 | 8/1990 | European Pat. Off. . |
| 0 560 728A1 | 9/1993 | European Pat. Off. . |
| 2 674 217 | 9/1992 | France . |

*Primary Examiner*—Elizabeth McKane
*Assistant Examiner*—Fariborz Moazzam
*Attorney, Agent, or Firm*—Finnegan, Henderson, Farabow, Garrett & Dunner, L.L.P

[57] ABSTRACT

A disinfection system and method for contact lenses that ensures that a disinfection liquid maintains its strength until the moment it is used. The system includes a lens case specially adapted to receive a prepackaged disposable container of disinfection liquid, the opening of which is provided with a tear-off seal to be removed immediately before use. The disposable container contains an amount of disinfection liquid suitable for one disinfection procedure for a set of contact lenses. The use of the disposable container system obviates bacterial growth in the container of the lens case.

8 Claims, 3 Drawing Sheets

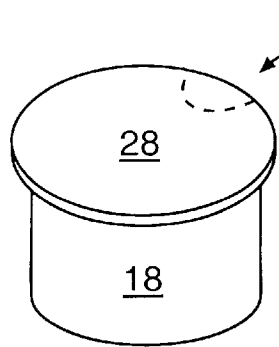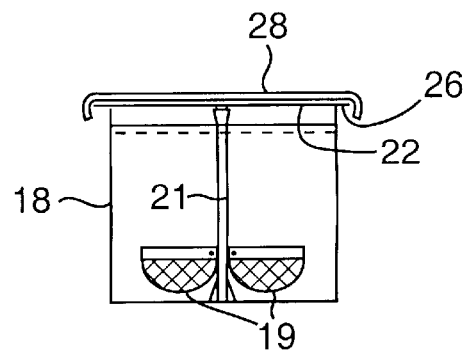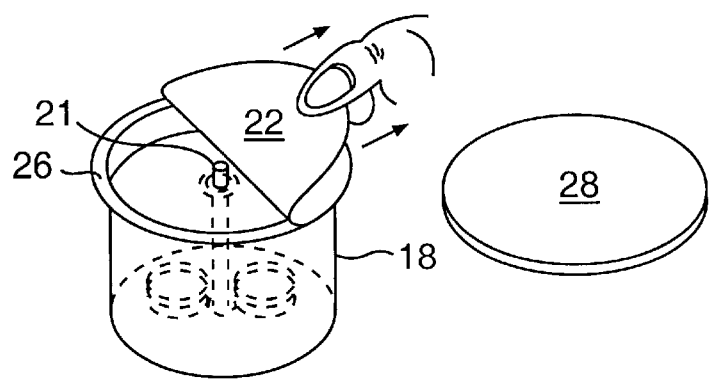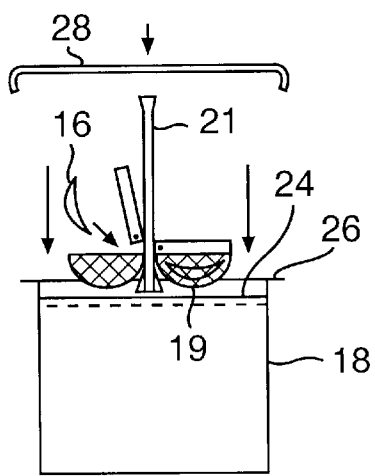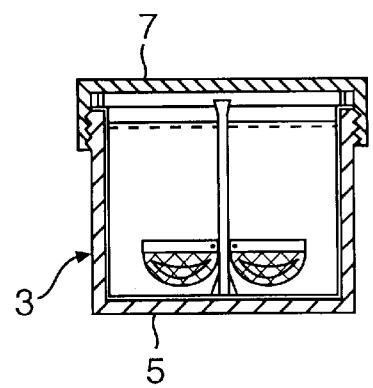

DISINFECTION SYSTEM FOR DISINFECTION OF CONTACT LENSES

BACKGROUND OF THE INVENTION

The invention concerns a disinfection system for disinfection of contact lenses and comprising a sealed disposable package containing a suitable amount of disinfection liquid to disinfect a set of contact lenses.

Users of contact lenses are aware that, at best, contact lenses are to be cleaned and disinfected daily to avoid trouble in use.

In practice, disinfection of contact lenses takes place in that a disinfection liquid from a container is poured into a specially designed lens case in which the cleaning process takes place. The lens case consists of a lens holder with a lens basket usually secured to the underside of the lens case lid as well as a container to receive disinfection/neutralization liquid onto which the lid may be screwed. When the contact lenses have been placed in the lens baskets, the lens case lid is screwed on the case, whereby the lens baskets with the contact lenses are immersed into the disinfection liquid in the container and are thereby cleaned.

Various types of liquids are used for cleaning contact lenses, depending on the cleaning system used by the user. One of the systems comprises the use of two liquids, the method comprising first immersing the lenses into hydrogen peroxide ($H_2O_2$), which is a very strong disinfecting and cleaning liquid. After the disinfection, the lenses are immersed into a neutralization liquid, and then the contact lenses are ready for use. Sometimes the users of this system forget how far they have gone in the cleaning process, and since the neutralization liquid has the same color as the hydrogen peroxide solution, the user may be easily mistaken or his memory may be at fault, and consequently there have been several cases where the user, believing that the lenses had been neutralized, has then inserted them in the eye directly from the hydrogen peroxide solution, which is very painful.

To avoid such unfortunate actions, DK Patent No. 168 746 B1 proposes a cleaning system where the contact lenses are immersed into a two-compartment case with hydrogen peroxide, but where the case contains a third compartment which communicates with the two compartments and in which a soluble tablet containing a neutralization agent (catalase) is placed. The gradual dissolution of the tablet neutralizes the hydrogen peroxide solution so that the contact lenses will be disinfected and neutralized when the tablet has been dissolved completely after a certain period of time. However, a drawback of this disinfection system is that sometimes the user forgets to place the tablet in the case, so that the contact lenses are inserted without having been neutralized. Another risk is that the user inserts the contact lenses before the tablet has been dissolved completely and the hydrogen peroxide solution has not been neutralized completely.

Today, all-in-one liquids have been developed for simultaneous cleaning, disinfection and insertion of contact lenses, the idea being to take the lens directly from the disinfection liquid and to insert it in the eye. The disinfection agent in these liquids is relatively weak, since otherwise, it would disturb the environment of the eye and cause allergic reactions, because the lenses are not neutralized before being inserted. The all-in-one liquids are supplied in containers/bottles containing up to 360 ml, sufficient for two months, consumption, if the lenses are disinfected daily. In practice, 360 ml are frequently enough for more than two months, as the user saves or just uses the contact lenses at intervals. Health authorities have generally recommended smaller container sizes, corresponding to one month's consumption, it being desired to reduce the risk of bacterial growth in the container. Frequently, the container is stored in bathrooms with many bacteria and fungi, and the users frequently forget to screw the lid onto the container after use. An American study (Donzis) has shown bacterial growth in 11–66% of the containers.

The bacterial growth in the containers reduces the effect of the disinfection agent, weak as it is, so that its disinfecting effect is already reduced before it gets into contact with the contact lenses. The disinfection of the contact lenses will thus be incomplete, whereby the eye will be liable to infection.

The conclusion has been that the safest form of a package of all-in-one liquids is a disposable bottle, commonly called a unit dose, having a ml content corresponding precisely to that needed for one disinfection procedure. Such containers containing 15 ml are known, but are relatively expensive, and their bottle-like shape enables the user to use one half and to save the rest for the next day, which involves a risk of bacterial growth.

The previously mentioned lens case is used for disinfecting contact lenses with the all-in-one liquids and is thus a decisive element of the actual disinfection process. Because of the ability of bacteria to form their own protecting bio film, it is difficult to keep the lens case clean, and today it is therefore recommended to exchange the case as frequently as every month.

Exchange every three months is perhaps acceptable, if the user uses a strong disinfection agent, e.g., 3% hydrogen peroxide, which, however, requires neutralization of the disinfection agent and the lens before the lens is inserted.

Studies (Donzis) have shown that bacterial growth in lens cases differs significantly, depending on the disinfection agent used, within three weeks, use of a new case. If the hydrogen peroxide system is used, there is no bacterial growth within the first three weeks. If, however, all-in-one systems are used, growth occurs in 25% of the cases within the first 21 days. Thus, with bacterial growth in the case, the situation is quite different when using a so-called all-in-one system as the disinfection system.

The conclusion of the study is that if an all-in-one disinfection system is used, it is very important to maintain the effect of the disinfection agent during storage in the container by the user. Further, it is very important to use a sufficient and correct amount of a disinfection agent to disinfect the contact lenses. In addition, the lens case is to be exchanged, or sterilized in another manner to avoid reducing the effect of the disinfection agent in relation to the lens with the consequent risk of eye infection.

EP A1 381 616, EP A1 401 163 and FR A1 2 674 217 disclose disposable systems for cleaning contact lenses.

EP A1 381 616 concerns a disposable system for cleaning contact lenses, which comprises a first container to receive contact lenses and a second container containing a sterilization or disinfection agent. The first container has a means to pierce the lid on the second container when the second container is folded over the first container. The container with contact lenses contains a catalyst to degrade the sterilization agent.

EP A1 401 163 concerns a disposable system comprising two pairs of containers. The first pair contains a sterilization agent, and the second pair contains a neutralization agent. Contact lenses are cleaned by first placing the lenses in their respective containers with a sterilization agent and then transferring the lenses to the containers with a neutralization agent. The system may be provided with a lid, if the lenses are to be stored in the system for an extended period of time. Further, the system may be provided with a spoon-like means to handle the lenses.

FR A1 2 674 217 concerns a disposable container containing a cleaning liquid. In use, the lid of the container is removed by breaking a fragile area, and then the lenses are placed in the liquid. The lid may be applied to the container again.

Further, U.S. Pat. No. 5,375,698 discloses a contact lens container which is constructed with a base member having at least one compartment and provided with a laterally projected flange around the perimeter of the base member, a reusable adhesive is deposited on the projecting flange and a cover sheet member, extending at least across the full length and width of the compartment, is releaseably united to the base member at the flange by the adhesive and thus forming a fluid-tight seal.

These disposable systems have a number of drawbacks:

The lenses are to be handled either by the fingers or by a spoon-like means, which makes handling risky and lens damage likely.

The disposable systems are restricted either to all-in-one liquids or to two-liquid disinfection systems.

The disposable systems are made of a fragile material, which makes them mechanically unstable during transport (risk of leakage).

It is likely that the lenses are discarded together with the disposable system, as the lenses are difficult to see when they are present in the liquid.

SUMMARY OF THE INVENTION

The object of the invention is to provide a method of disinfecting contact lenses in a lens case filled with a disinfection liquid, where the contact lenses optionally are placed in a lens basket of a case suspended, e.g., from a case lid and down in the disinfection liquid when the lid is screwed onto the container, obviating the above-mentioned drawbacks, to ensure that the lens user uses the correct amount of disinfection liquid, and to ensure that the effect of the disinfection liquid is maintained until the moment when it contacts the contact lenses.

This object is achieved by a new distribution principle which radically departs from the traditional principles, where disinfection takes place in a disposable container, which is made of a fragile material, where handling of the contact lenses is very risky, e.g., by the fingers and where good control of the lenses is not possible.

The new distribution principle uses a new disinfection system to disinfect contact lenses, comprising a sealed disposable container containing a suitable amount of disinfection liquid to disinfect a set of contact lenses, said disposable container being formed with a wide mouth suitable for receiving holding means for contact lenses, characterized in that the disposable container is used as an insert in a container of a lens case. Thus, in addition to serving as a distribution unit in the form of a disposable package, the disposable container also serves as a disinfection container/vessel in connection with disinfection of contact lenses. With the new principle, both the disinfection liquid and the disposable container are exchanged after completed disinfection of the contact lenses, thereby eliminating the risk of bacterial growth in the container in which the disinfection takes place, and allowing the disinfection liquid to maintain its optimum effect until the moment when the seal on the disposable container is torn off and the lens baskets with the contact lenses are immersed into the disinfection liquid. Another advantage of the new disinfection principle is that when using disposable containers it ensures that the lens user uses the correct amount of disinfection liquid to disinfect the contact lenses.

At its opening, the disposable container is provided with an annular flange having an upper side to which a tear-off sheet seal is attached. This attachment method, providing a good contact face between the sheet and the flange, ensures that the disinfection liquid is protected effectively against bacterial attacks during storage until use. The flange moreover has several other functions, which will be mentioned below.

When the disposable container can also accommodate a means to receive the contact lenses or holding means for them, it is additionally ensured that the contact lenses may be effectively disinfected, and following disinfection of the contact lenses, it is moreover possible—in addition to exchange of disinfection liquid and the container in which the disinfection process takes place—to exchange the lens baskets more frequently than in the use of the traditional lens cases. The frequent exchange of the lens baskets means that they will not be infected by bacteria before they are exchanged. When the lens baskets are stored in the disposable containers containing disinfection liquid, the lens baskets may be considered to be sterile until the moment when the seal is torn off.

When the means to receive the contact lenses are formed by disposable lens baskets, the use of the disinfection system of the invention ensures the contact lenses may always be disinfected in an environment which is not infected by bacteria beforehand.

When the means to receive the contact lenses are arranged on a stem whose free end protrudes from the disinfection liquid level, it is ensured that contact between the user's fingers and the disinfection liquid in the disposable container is reduced to a minimum.

Also, the disposable container may be constructed such that it may be placed as a disposable insert in a container of a lens case, following which the seal across the opening is torn off prior to the mounting of the lid with the lenses in the lens baskets. The additional advantages of this are that the lens case container, which usually is a cylindrical transparent container of impact-proof plastics, and which takes more resources to manufacture than the disposable container, does not have to be exchanged with the common frequency, as it does not contact the disinfection liquid and is thus not subjected to bacterial attacks. Further, the lens case container is used for protecting the disposable container.

The disposable container of the invention containing means to receive the contact lenses or holding means (disposable lens basket) for this finds application as an insert in primitive lens cases which do not comprise a lens basket.

The protruding flange on the disposable container, provides a tight connection between the lid of the lens case and the disposable container, so that the container of the lens case is not contaminated by bacteria from the contact lenses, as the interior thereof does not get in contact with the disinfection liquid of the disposable container. The container of the lens case is thus used for securing and protecting the disposable container in the correct position below the lens baskets, as well as an additional protection against bacterial attacks.

The disinfection system of the invention is, moreover, extremely useful in connection with the use of the system, comprising a first cleaning in hydrogen peroxide ($H_2O_2$) and a subsequent neutralization in a neutralization liquid, as the user is always certain of how far he has proceeded in the disinfection process, since the disposable containers are discarded as they are used. Thus, if the contact lenses are being disinfected in $H_2O_2$, the disposable container containing the neutralization liquid will be juxtaposed with an unbroken seal, thereby enabling it to be observed that the neutralization process has not been completed. A further safeguard against wrong use of disinfection liquid and neutralization liquid may comprise providing the disposable containers for the respective liquids with mutually different colors and/or shapes. This minimizes the risk of inserting non-neutralized contact lenses when using the disposable containers according to the invention.

The containers containing $H_2O_2$ and neutralization liquid, respectively, may have different shapes and appearances, and the upper sides of the seals thereof may be provided with marks clearly indicating what the containers contain, thereby reducing the risk of mistakes.

Of course, the disposable containers are relatively small, as they are intended to be accommodated in the container part of the lens case. This means that they occupy very little space, and as a result the new distribution system, in addition to the advantages already mentioned, also have the same advantages with respect to space requirements as the known all-in-one disinfection liquids that are supplied in unit dose packages.

BRIEF DESCRIPTION OF THE DRAWINGS

The invention will be explained more fully below with reference to the drawing, in which FIG. 1 is a perspective view of an unopened disposable container with a lid, FIG. 1A is lateral sectional view of FIG. 1, containing disposable lens baskets, FIG. 2 is a perspective view of FIG. 1A, with partly a removed seal, FIG. 3 is an exploded lateral view of FIG. 2 during insertion of contact lenses into the disposable lens baskets, FIG. 3A shows the disposable container used as an insert in a simple lens case.

DESCRIPTION OF THE PREFERRED EMBODIMENTS

Figure 4:
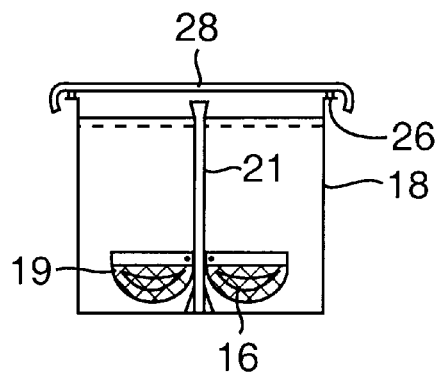
FIG. 4 is a lateral sectional view of the disposable container in an assembled state.

The disinfection system 1 of the invention is shown in FIG. 1 in an unopened state and comprises a disposable container 18 with a tear-off sheet seal 22 secured on an annular flange 26 (FIG. 2). The disposable container 18 is formed with a mouth wide enough to receive holding means 14, 19 for contact lenses 16 during the disinfection process.

As shown in FIG. 1A, a removable, tight-fitting lid 28 may be provided along the rim of the disposable container above the sheet seal 22. Further, the disposable container 18, in addition to the disinfection liquid 24, may also contain a set of lens baskets 19 secured to a stem 21, whose free end protrudes above the disinfection liquid level.

When the disinfection system 1 is to be used, the lid 28 is removed from the disposable container 18, and then the sheet seal 22 is torn off (FIG. 2). Then, the stem 21 is grasped by the finger tips and the lens baskets 19 are lifted out of the disposable container 18. The contact lenses 16 are then placed in the lens baskets 19, as appears from FIG. 3, which, in turn, are immersed into the disposable container 18 by again grasping the free end of the stem 21 by the finger tips. The lid 28 is applied over the opening of the disposable container (FIG. 4), and the disinfection process takes place.

The disposable container 18 may also be used as an insert in a simple lens case 3, without a lens basket, as appears from FIG. 3A. This embodiment of the disinfection system does not comprise the lid 28, the protruding flange 26 on the disposable container 18 being clamped between the rim of the lens case 5 and a sealing member 13, cooperating with it, in the form of an O-ring seal on the lid 7 of the lens case. Placing of the contact lenses 16 in the lens baskets 19 in connection with the disinfection process takes place as described before.

Figure 5:
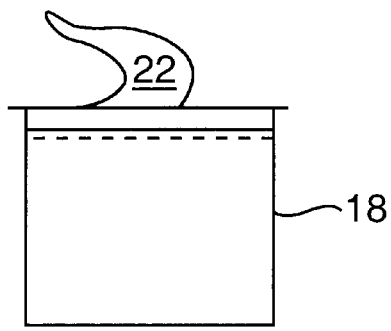
FIG. 5 shows the disposable container during removal of the tear-off sheet.
Figure 6:
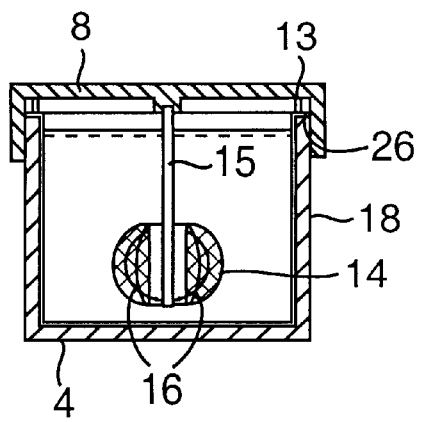
FIG. 6 is a lateral sectional view of the disposable container used as an insert in a normal lens case.

The embodiment of the disinfection system 1 shown in FIG. 5 for use together with traditional lens cases, with lens baskets 14 secured to a stem 15 whose free end is secured in the lens case lid 8, comprises a disposable container 18 with the tear-off sheet seal 22 described before. In use, as disclosed in FIG. 6, the disposable container 18 is placed in the container 4 of the lens case, before or after the sheet seal 22 is torn off. The contact lenses 16 are then placed in the lens baskets 14, and the lid 8 is applied to the container 4, whereby the lens baskets 14 containing the contact lenses 16 are immersed into the disinfection liquid 24. Application of the lid 8 causes the protruding annular flange 26 to be clamped between the rim of the container 4 and a sealing member 13, cooperating with it, in this case an O-ring on the lid 8.

Figure 7:
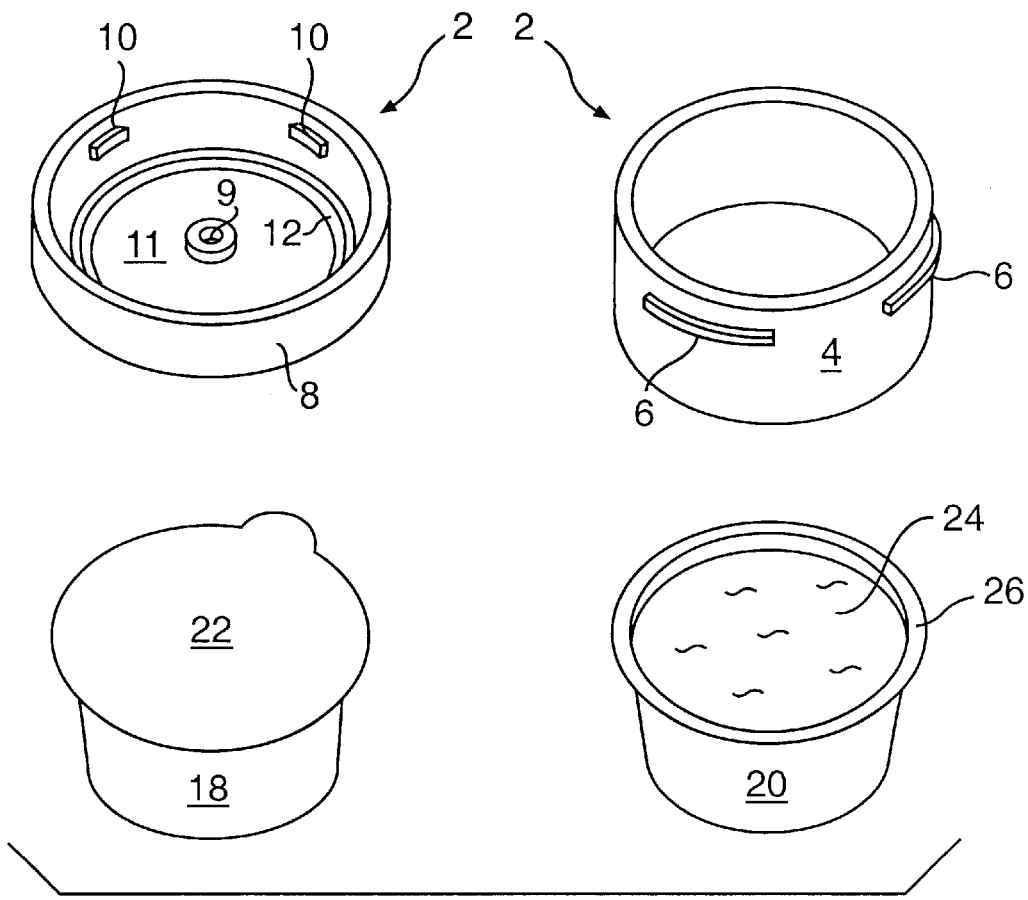
FIG. 7 is a perspective view of a lens case to receive disposable containers.

A lens case 2 for use together with the disinfection system 1 of the invention is shown in a disassembled state in FIG. 7. The lens case 2 consists of two main parts, a container 4 whose external rim has bayonet threads 6 to enable the lid 8 to be screwed on.

Figure 8:
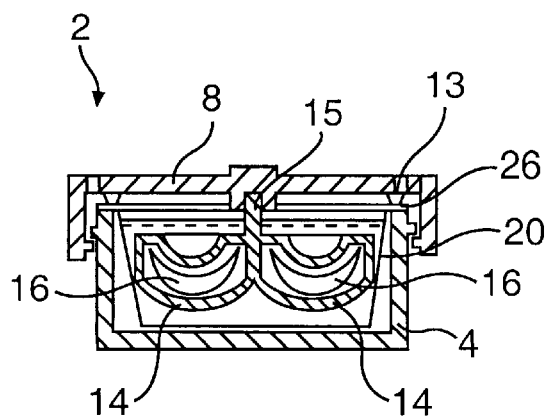
FIG. 8 is a lateral sectional view of a lens case with an inserted disposable container during cleaning of contact lenses.

As appears in FIG. 7, the inner side of the lid 8 has a plurality of gripping flaps 10 intended to engage the bayonet threads 10 on the container 4. An inner side 11 of the bottom of the lid is formed with an annular groove 12 in which a seal 13, in this case an O-ring, of a suitable material is embedded. The O-ring 13 is so positioned in the lid 8 that when the lid is screwed onto the container 4, the O-ring engages the upper edge of the container. As appears in FIG. 8, the underside of the lid 8 has two lens baskets 14 carried by a stem 15 which is inserted into the central hole 9 of the lid, said baskets being intended to receive a set of contact lenses 16. When the lid 8 is screwed firmly onto the container 4, the lens baskets 14 extend down into the interior of the container.

FIG. 7 additionally shows two containers 18, 20 in the shape of a cup having an annular flange 26 along the rim. One container 18 has an intact seal in the form of a tear-off sheet 22. The tear-off sheet 22 is removed on the other container 20, which contains disinfection liquid 24. The cups 18, 20 are shaped such that they may be received in the container 4, so that the annular flange 26 engages the upper edge of the container. In the applied position of the case lid 4, the O-ring engages the annular flange 26 on the disposable container 20 (FIG. 8), thereby forming a tight connection between the container 20 and the lid 8. In the same position, the lens baskets 14 extend down into the liquid in the container 20.

Disinfection of contact lenses 16 takes place by placing them in the lens baskets 14, following which, the disposable container 20 is placed in the container 4, and the sheet 22 across the mouth on the disposable container 20 is torn off. The lid 8 is then threaded onto the container, thereby causing the lens baskets 14 containing the contact lenses 16 to be immersed into the disinfection liquid 24 which is present in the container 20, and which has maintained its optimum effect till now. After treatment is completed, the lid 8 is screwed off the container 4, and the disposable container 20 with the spent liquid is discarded. If a two-liquid disinfection system is used, the container with the neutralization liquid is then inserted into the container 4 after tearing-off of the disposable sheet 22, and the lid 8 is screwed on again, following which the neutralization process takes place.

If the user of the contact lenses is particularly careful with the cleaning of his lenses, the lenses are rubbed before being disinfected. The mechanical action results in a better cleaning of the bacterial film and of other impurities on the lenses than the disinfection which takes place merely by immersing the lenses into disinfection liquid. A little liquid is necessary for the rubbing, which is performed by a finger. The spent liquid from the preceding disinfection may be used for this purpose, or sterile brine. As the lid and container of the lens case are sealed, it is thus possible to store the liquid after the disinfection until rubbing is to be performed. After rubbing, the disposable container with the spent liquid is discarded, a new one is inserted, and the actual disinfection of the contact lenses takes place.

It is common to the use of the disinfection system 1 of the invention that both the disposable container 18 and the spent disinfection liquid 24 present in the container are discarded after the completion of the disinfection of the contact lenses 16.

If the disinfection system 1 also comprises holding means in the form of lens baskets 19 as well as a cover 28, these parts are discarded together with the container 18 and the spent disinfection liquid 24. If the user does not want to exchange the cover 28 and the lens baskets 19 after each disinfection of contact lenses, these parts may be used again together with the embodiment of the disinfection system which does not comprise these parts. Hereby, the precise exchange frequency of lens baskets 19 and cover 28 desired by the user, may be achieved.

As an additional safeguard against contamination in connection with the disinfection process, the cover 28 may also be provided with a tear-off film on the side facing the container mouth, said film being removed immediately before the application of the cover on the container.

Thus, the described disinfection system provides a method of ensuring that the correct amount of disinfection liquid is used for the disinfection of contact lenses, thereby eliminating the danger of bacterial growth in the case container.

The use of the method and the lens case of the invention in connection two two-liquid disinfection systems reduces the risk of inserting non-neutralized contact lenses practically to zero, as the user can always observe how far he is in the cleaning process on the basis of the shape and color of the containers.

If the disposable containers, containing $H_2O_2$ and neutralization liquid, respectively, are made of a material of different appearance and/or shape, e.g., with different colors, the risk of inserting non-neutralized contact lenses is reduced additionally, as the user, by looking at the disposable container, can see what it contains, e.g., a red container contains $H_2O_2$, and a green container contains neutralization liquid. The different container colors are relevant particularly where the user has torn off the seal on both containers at the same time, it being of paramount importance to the user to know which container contains which.

What remains is thus how to keep the lid 8 and the lens baskets 14 free of bacteria in the lens case 2 for use together with the disinfection system 1. However, exchange of the baskets will hardly be necessary, as the disinfection takes place in liquid with unreduced strength. As an additional safeguard, the lid 8, the O-ring 13 and the lens baskets 14 may be made of a material resistant to boiling, thereby allowing these to be boiled, optionally in a weak brine solution, which kills the bacterial cultures that might have survived the disinfection with the disinfection liquid.

The disposable containers may be made with a quite small thickness in an inexpensive manner, e.g., as vacuum formed sheet elements, as these will be protected by the container of the lens case in use. Further, they are usually supplied in multi-unit boxes with a suitable strong package optionally formed as a dispenser, or suitable in such a one, suspended from a wall or the like.

It is contemplated that the containers 18 of the disinfection system and the lens baskets 19, 14 as well as the special lens case 2 may be made of recyclable plastics materials to the greatest possible extent.

I claim:

1. A disinfection system for immersing contact lenses in a liquid, comprising a lens case, having a container and a tight-fitting container lid, and a disposable prepackaged container of the liquid receivable as an insert in the container of the lens case.

2. A disinfection system according to claim 1, wherein the disposable container has an opening surrounded by an annular flange having an upper side, and a tear-off sheet seal attached to the upper side of the annular flange in an unopened state of the disposable container.

3. A disinfection system according to either of claims 1 and 2, wherein the disposable container includes means for receiving and holding the contact lenses.

4. A disinfection system according to claim 3, wherein the means for receiving and holding the contact lenses include a set of disposable lens baskets on a stem having a free end protruding above the liquid in the disposable container.

5. A disinfection system according to either of claims 1 and 2, wherein the container lid includes lens baskets extending down into the container of the case when the lid is mounted to close the case.

6. A disinfection system according to claim 2, wherein the annular flange of the disposable container is optionally clamped between a rim of the container of the lens case and a cooperating sealing member on the lid container.

7. A disinfection system according to any one of claims 1, 2 and 6, including separate disposable prepackaged containers of a disinfection liquid and a neutralization liquid, respectively, the separate disposable containers having distinguishable colors or shapes.

8. A disinfection system according to claim 7, wherein each of said disposable containers contain a disinfection liquid in an amount restricted to a single disinfection of one set of contact lenses and having an opening of a width to receive holding means for the set of contact lenses.

* * * * *